(12) United States Patent
Giese

(10) Patent No.: US 7,726,331 B1
(45) Date of Patent: Jun. 1, 2010

(54) MODULAR FLUID HANDLING DEVICE II

(76) Inventor: Gregory C. Giese, P.O. Box 5617, Madison, WI (US) 53705

( * ) Notice: Subject to any disclaimer, the term of this patent is extended or adjusted under 35 U.S.C. 154(b) by 623 days.

(21) Appl. No.: 11/752,511

(22) Filed: May 23, 2007

(51) Int. Cl.
*F16K 11/20* (2006.01)

(52) U.S. Cl. ............ 137/269; 137/884; 285/124.5

(58) Field of Classification Search ......... 137/269, 137/270, 271, 884; 285/124.5, 124.1
See application file for complete search history.

(56) References Cited

U.S. PATENT DOCUMENTS

| | | | |
|---|---|---|---|
| 1,061,142 | A | 5/1913 | Tesla |
| 3,831,953 | A | 8/1974 | Leibfritz et al. |
| 4,218,176 | A | 8/1980 | Gawne |
| 4,947,695 | A * | 8/1990 | Lohr ............... 73/863.01 |
| 4,971,771 | A | 11/1990 | Stahl |
| 5,341,768 | A | 8/1994 | Pope |
| 5,385,712 | A | 1/1995 | Sprunk |
| 5,841,036 | A | 11/1998 | Mayeaux |
| 6,749,814 | B1 | 6/2004 | Bergh et al. |
| 6,818,183 | B2 | 11/2004 | Hajduk |
| 6,824,577 | B2 | 11/2004 | Deshpande |
| 7,146,999 | B2 | 12/2006 | Giese et al. |
| 7,455,088 | B2 * | 11/2008 | Hirschburger et al. .. 144/136.95 |
| 2001/0006611 | A1 | 7/2001 | Koski et al. |
| 2002/0001538 | A1 | 1/2002 | Hajduk et al. |
| 2004/0018124 | A1 | 1/2004 | Filippi et al. |
| 2004/0136873 | A1 | 7/2004 | Meier |

OTHER PUBLICATIONS

ANSI/ISA-76.00.02-2002, Modular Component Interfaces for Surface-Mount Fluid Distribution Components—Part 1: Elastomeric Seals; Instrumentation, Systems, and Automation Society (2002).
Bauer et al., Development of a rapid prototyping process chain for the production of ceramic microcomponents, *Journal of Materials Science*, 37:3127-3140 (2002).
CPAC NeSSI website, New Sampling/Sensor Initiative (NeSSI™), http://www.cpac.washington.edu/NeSSI/NeSSI.htm (2005).
NeSSI™ (New Sampling/Sensor Initiative) Generation II Specification (2003-2004).

* cited by examiner

*Primary Examiner*—Kevin L Lee
(74) *Attorney, Agent, or Firm*—Craig A. Fieschko, Esq.; DeWitt Ross & Stevens S.C.

(57) ABSTRACT

A modular fluid handling device includes at least one block having opposing block faces shaped as tessellating regular polygons, and a series of block sides therebetween. Each block includes a central bore and fluid passages extending between the block faces, and possibly ducts extending between the bore and the fluid passages. The blocks may be rapidly horizontally and/or vertically affixed with their bores and/or fluid passages in communication to form a fluid handling device having the desired configuration (e.g., with the bores and fluid passages forming a desired process flow path, fluid circuit, or the like). Star wheels and/or rotor discs can be provided within the block bores for purposes of pumping fluids flowing within the bores, and/or for purposes of deriving power from fluid flow within the bores.

20 Claims, 3 Drawing Sheets ns have their
MODULAR FLUID HANDLING DEVICE II

FIELD OF THE INVENTION

This document concerns an invention relating generally to devices for processing and sampling of gases and liquids, and more specifically to devices allowing rapid construction of fluid reactors, distillers, extractors, homogenizers, filtration/separation devices, process models (e.g., devices for modeling engine cycles, refrigeration cycles, etc.), and other devices for handling fluids.

BACKGROUND OF THE INVENTION

Fluid handling devices including fermenters, distillers, filtration tanks, evaporators, etc. (or combinations of these components) are exceedingly common in industry and in research labs. Researchers and engineers also often need to experiment with models for common thermodynamic cycles, e.g., refrigeration cycles (vapor compression cycle, Einstein cycle, etc.) and power cycles (Otto cycle, Diesel cycle, Brayton cycle, Rankine cycle, etc.). While it is often desirable to generate prototypes or small-scale versions of such devices, they are usually time-consuming, difficult, and expensive to construct. One approach commonly used in laboratories is to connect glassware vessels (e.g., flasks, towers, heat exchangers, etc.) with rubber tubing so that the vessels form some desired fluid process model. Even apart from the significant time and expense required for their construction, these are quite fragile, are unsuitable for pressurized processes, and are also usually unsuitable for processes involving extreme temperatures or corrosive materials owing to the weakness of the tubing. In some cases, more durable fluid handling devices can be formed from metal vessels connected with (for example) brazed copper tubing, but these involve even greater time, cost, and fabrication burdens.

A prior patent (U.S. Pat. No. 7,146,999 to Giese et al., which is incorporated by reference herein) describes a modular fluid handling system wherein modular blocks bear passageways for carrying fluids, and wherein inserts having different functionality—e.g., valve inserts, filter inserts, turbine inserts, pump inserts, heating/cooling inserts, sensor inserts, flow routing/diverting inserts, etc.—can be inserted into selected blocks. The blocks, with or without inserts, can be affixed together to construct a durable fluid handling device. This document relates to improvements and additions to the modular fluid handling system described in U.S. Pat. No. 7,146,999 to Giese et al.

SUMMARY OF THE INVENTION

To enhance the reader's understanding, the following summary will make reference to the accompanying FIGS. 1-3, which illustrate an exemplary version of the modular fluid handling device. The device includes a number of blocks—more particularly, fluid passage blocks 100 and fluid intake/outlet blocks 200, as will be discussed below—which each include a block top face 102/202, an opposing block bottom face (not shown), and a series of block sides 104/204 therebetween. The block faces 102/202 are preferably shaped as tessellating regular polygons, whereby the blocks 100/200 may be arrayed together in side-to-side abutting relationship to form a two-dimensional array of blocks (as best seen in FIG. 1). Each block 100/200 includes a central block bore 106/206 extending between the block faces 102/202, whereby the blocks 100/200 may also (or alternatively) be arrayed together in face-to-face abutting relationship to form a stacked array of blocks wherein abutting blocks have their block bores 106/206 coaxially aligned (as seen in the stack of blocks 100/200 shown at the left side of FIGS. 1-3). The foregoing arrangement allows a user to horizontally array and vertically stack blocks 100/200 together into some desired arrangement which is suitable for the user's intended use, e.g., for purposes of experiment, prototyping, or production.

The blocks 100/200 include some means for allowing horizontally adjacent blocks 100/200 to be affixed together, with a preferred horizontal affixment means being best seen in FIG. 3. Here, the block faces 102/202 include semi-annular depressions 108/208 extending from the block sides 104/204, whereby adjacent blocks 100/200 arrayed together in side-to-side abutting relationship may receive an annular side fastener 300 in their adjacent semi-annular depressions 108/208 to affix the adjacent blocks 100/200 together.

The blocks 100/200 additionally include some means for allowing vertically stacked blocks 100/200 to be affixed together, with a preferred vertical affixment means being best seen in FIGS. 2-3. The blocks 100/200 here include face fastener openings 110/210 in their block faces 102/202, with the face fastener openings 110/210 being situated such that blocks 100/200 situated in face-to-face stacked relationship have their face fastener openings 110/210 coaxially aligned. This arrangement allows the blocks 100/200 to be affixed together in face-to-face abutment by extending a fastener 302 between the aligned face fastener openings 110/210 of the abutting blocks 100/200.

To provide a stable base for a fluid handling device assembled from a series of blocks 100/200, a mounting plate 304 is preferably provided upon which the affixed blocks 100/200 may rest. The mounting plate 304 has a mounting surface with plate fastener openings 306 arrayed therein, such that when several blocks 100/200 are received thereon in side-to-side abutting relationship, the plate fastener openings 306 coaxially align with the block face fastener openings 110/210. Fasteners 302 can then be extended through the block face fastener openings 110/210 and into the plate fastener openings 306 to affix a block to the mounting plate 304.

One or more of the blocks then takes the form of a fluid passage block 100 (see particularly FIGS. 2-3), wherein each fluid passage block 100 further includes one or more fluid passages 112 which extend between the opposing block faces 102, and which are situated between the block bore 106 and the block sides 104. These fluid passages 112 are preferably regularly arrayed about the block bore 106 such that a stacked array of fluid passage blocks 100 having their block bores 106 coaxially aligned will also have their fluid passages 112 coaxially aligned, such that fluid may travel between the fluid passages 112 of adjacently stacked fluid passage blocks 100.

One or more of the blocks also preferably takes the form of a fluid intake/outlet block 200 which includes the features of a fluid passage block 100 (i.e., it includes fluid passages 212 similar to the fluid passages 112 described above), but also includes ducts 214 extending from the fluid passages 212 to the block bore 206, whereby fluid may travel between the fluid passages 212 and the block bore 206. These ducts 214 may assume a variety of forms, but are preferably formed as shown in FIGS. 2-3, wherein the ducts 214 are defined as slotted openings which extend from the block bore 206 to the fluid passages 212. These ducts 214 are preferably oriented in directions extending both radially and tangentially with respect to the block bore 206, and which also extend between the opposing block faces 202 in a direction oriented along the axis of the block bore 206. By orienting the ducts 214 in an at least partially tangential direction (i.e., in an at least partially clockwise or counterclockwise direction), and by providing all ducts 214 with the same tangential orientation, fluid flowing from the fluid passages 212 to the block bore 206 (or conversely flowing from the block bore 206 to the fluid passages 212) will assume a circular or whirling motion in the block bore 206, which is useful for reasons discussed below.

The arrangement described above provides for axial flow of fluid between stacked blocks through the block bores 106/206 and/or fluid passages 112/212 (and ducts 214), as well as radial flow within a fluid intake/outlet block 200 between the fluid passages 212 and block bores 206 via the ducts 214. Fluid flow between horizontally adjacent blocks 100/200 can also be provided by channels—exemplified by channel 116—which extend from a block bore 106/206 to a block side 104/204, so that fluid may flow between adjacently aligned channels 116 in adjacent blocks. (Since only a single such channel 116 is illustrated in the accompanying drawings, the channel 116 can be regarded as a fluid input port, or a fluid output port, for its fluid passage block 100 to allow entry or exit of fluid to the stacked blocks 100/200.) Additionally, plugs may be provided in block bores 106/206 and/or in fluid passages to block the passage of fluid where desired. As best seen in FIGS. 2-3, bore plugs 308 are situated within the block bores 106 of the top and bottom fluid passage blocks 100 of the stack to prevent fluid flow within these block bores 106, and passage plugs 310 are provided within the fluid passages 112 of selected fluid passage blocks 100 to prevent fluid flow within these fluid passages 112. With the arrangement depicted in the drawings, it can be seen that fluid entering the channel 116 will flow into the central block bore 106 of its fluid passage block 100, up the block bores 106 of the fluid passage blocks 100 stacked above, into the block bores 206 of the fluid intake/outlet blocks 200 stacked above, and then into the ducts 214 and fluid passages 212 of these fluid intake/outlet blocks 200. The fluid can then exit the fluid passages 112 of the fluid passage block 100 at the top of the stack. (It should be understood that this is only an exemplary fluid flow arrangement, and that by arraying blocks 100/200 differently, different arrangements can be obtained.)

Various components may then be provided to allow pumping of fluid through the fluid passage blocks 100 and/or fluid intake/outlet blocks 200, or to allow fluid power to be derived from fluid flowing through the fluid passage blocks 100 and/or fluid intake/outlet blocks 200. An elongated shaft 312 (FIG. 3) may be centrally mounted within the block bores 106/206 of one or more blocks to extend along the axes of the block bores 106/206. As best shown in FIG. 3, the ends of the shaft 312 are mounted within the bore plugs 308 at the top and bottom fluid passage blocks 100 of the stack to maintain the shaft 312 at an orientation extending along the axes of the block bores 106/206 of the fluid passage blocks 100 and fluid intake/outlet blocks 200. The shaft 312 may then bear star wheels 400 and/or rotor discs 500—best seen in FIG. 3, wherein several star wheels 400 are shown stacked on the shaft 312 alongside a stack of rotor discs 500—to provide pump and/or turbine action. Each of the star wheels 400 and rotor discs 500 will now be discussed in turn.

Looking to FIG. 3, each star wheel 400 includes a central hub 402 with several vanes 404 extending therefrom, with opposing wheel faces 406 axially bounding the hub 402 and vanes 404 and an outer wheel circumference 408 radially bounding the vanes 404. The wheel circumference 408 is sized to be complementarily received within the block bore 106/206 of one of the blocks 100/200 so that a star wheel 400 may rotate within the block bore 106/206 with the wheel circumference 408 resting closely adjacent the walls of the block bore 106/206. A wheel bore 410 is centrally defined in, and extends between, the wheel faces to receive the shaft 312. Each star wheel 400 may therefore rotate about (or with) the shaft 312 as fluid flows within the block bore 106/206 to impel the vanes 404 in a circular direction, or to allow the vanes 404 to impel fluid in a circular direction. FIG. 3 illustrates the stack of star wheels 400 as having the vanes 404 of the star wheels 400 staggered within the stack, such that each star wheel 400 has its vanes 404 vertically bounded by the spaces between the vanes 404 of the adjacent star wheel(s) 400 (and conversely, each star wheel 400 has the spaces between its vanes 404 vertically bounded by the vane(s) 404 of the adjacent star wheels 400). As a result, fluid cannot flow vertically between adjacently stacked star wheels 400 unless apertures 412 are defined in the vanes 404, with the apertures 412 extending between the opposing wheel faces 406. The apertures 412 thereby allow fluid to flow vertically through a star wheel 400, as well as driving the star wheel 400 (or being driven by the star wheel 400) circularly within the block bore 106/206. The star wheels 400 need not have vanes 404 which are oriented solely in radial directions with respect to the wheel bore 410 (i.e., in "paddlewheel" fashion), and vanes 404 may be angled tangentially as well as radially (i.e., in "pinwheel" fashion), with all vanes 404 angled in clockwise or counterclockwise directions, to help impart the star wheels 400 with preferential directions of spin (at least at startup).

Also looking to FIG. 3, the rotor discs 500 each have opposing disc faces 502 axially bounding each rotor disc 500, an outer disc circumference 504 radially bounding the disc faces 502, and a disc bore 506 centrally defined in (and extending between) the disc faces 502 for receiving the shaft 312. The disc circumference 504 is preferably sized to be complementarily received within the block bore 106/206 of one of the blocks 100/200 so that a rotor disc 500 may rotate within a block bore 106/206 with the disc circumference 504 closely spaced adjacent the wall bounding the block bore 106/206. One or more disc fluid passages 508 are then situated between the disc bore 506 and the disc circumference 504 to extend between the opposing disc faces 502, thereby allowing fluid flow between the disc faces 502. As a result, when rotor discs 500 are stacked in spaced relation and fluid is directed axially through the disc fluid passages 508, with the fluid being able to flow radially outwardly between the spaced discs 500 (as it can in the accompanying drawings, wherein radially outwardly flowing fluid may exit the ducts 214 in the fluid intake/outlet blocks 200), the rotor discs 500 will be driven by the fluid to rotate owing to surface adhesion/boundary layer flow effects (a phenomenon noted by Nikola Tesla, and utilized to similar effect in Tesla's U.S. Pat. No. 1,061,142). Conversely, rotation of the shaft 312 and rotor discs 500 can be used to pump fluids.

To space the rotor discs 500 apart, spacers 314 are also preferably provided. Each spacer 314 has opposing spacer faces 316 which axially bound each spacer 314, an outer spacer circumference 318 radially bounding the spacer faces 316, and a spacer bore 320 extending between the spacer faces 316 wherein the shaft 312 may be received. The spacer circumference 318 is preferably sized with a radius less than the radius between the disc bore 506 and the disc fluid passages 508, so that a spacer 314, when situated on the shaft 312 between a pair of rotor discs 500, will not block fluid flow between the disc fluid passages 508 of the spaced discs 500.

By suitably arranging the foregoing fluid passage blocks 100 and fluid intake/outlet blocks 200 (as well as any of the blocks described in U.S. Pat. No. 7,146,999 to Giese), as well as plugs 308/310, shafts 312, star wheels 400, rotor discs 500, spacers 314, etc., a user can generate a wide variety of fluid pumping and/or fluid power arrangements. To illustrate, in the arrangement of the accompanying drawings, fluid may enter the channel 116, flow axially upwardly in the block bores 106 of the fluid passage blocks 100 and also upwardly through the vane apertures 412 of the star wheels 400 therein, and then flow axially upwardly within the block bores 206 of the fluid intake/outlet blocks 200. Within the fluid intake/outlet blocks 200, the fluid may flow through the disc fluid passages 508 of the rotor discs 500, as well as radially outwardly between the spaced rotor discs 500, to enter the ducts 214 and fluid passages 212 of the fluid intake/outlet blocks 200. The fluid may then exit the fluid passages 112 of the top fluid passage block 100. The fluid can either be driven along the foregoing paths if the shaft 312 and one or more of the star wheels 400 and rotor discs 500 are driven to rotate, or alternatively the fluid can drive the shaft 312, star wheels 400, and/or rotor discs 500 if a suitable pressure difference is present between the points of fluid input and output.

Further advantages, features, and objects of the invention will be apparent from the remainder of this document in conjunction with the associated drawings.

DETAILED DESCRIPTION OF PREFERRED VERSIONS OF THE INVENTION

Figure 1:
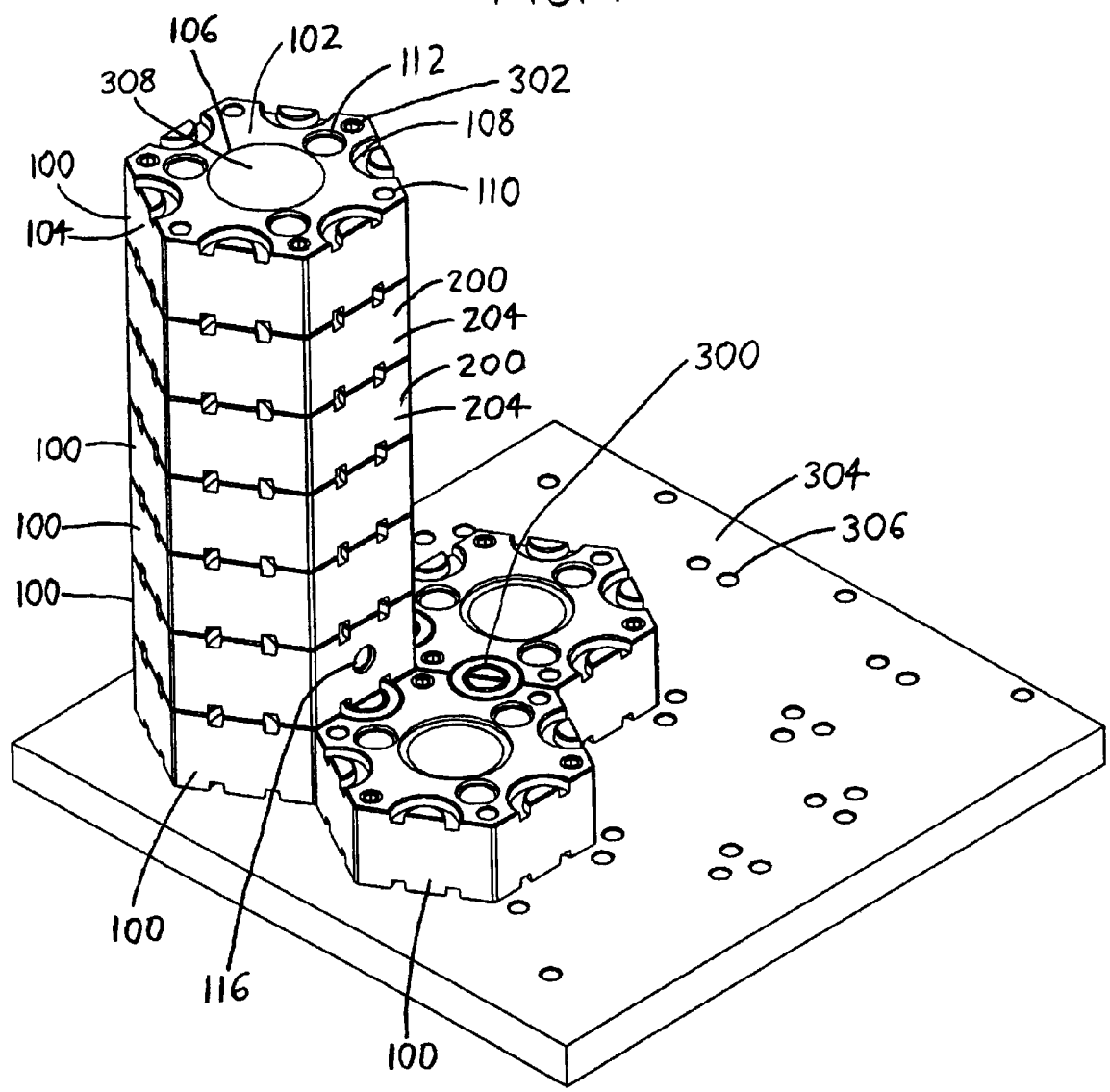
FIG. 1 provides a perspective view of an exemplary fluid handling device which illustrates concepts of the invention, wherein the aforementioned fluid passage blocks 100 and fluid intake/outlet blocks 200 are affixed together in a vertical stack via fasteners 302, and are also affixed together in a vertical array via annular side fasteners 300.

Expanding on the foregoing Summary, following are further details regarding exemplary and preferred versions of the invention.

Regarding the fluid passage blocks 100 and the fluid intake/outlet blocks 200, these are preferably formed of heat- and corrosion-resistant materials such as stainless steel, but other materials can be used. Block materials can be specially chosen to achieve desired objectives; for example, a block 100/200 could be formed of plastic or ceramic materials to reduce heat conduction, or of transparent plastic or glass to allow visualization of its contents, etc. A user could then choose an assortment of blocks 100/200 having desired characteristics, and assemble them to better fulfill the intended purpose of the fluid handling device. In this respect, it is emphasized that a fluid handling device need not include only the fluid passage blocks 100 and the fluid intake/outlet blocks 200 discussed above, and that other types of modular blocks—such as those described in U.S. Pat. No. 7,146,999 to Giese et al. (which is incorporated by reference herein)—may be used with the fluid passage blocks 100 and/or the fluid intake/outlet blocks 200. It should further be understood that the blocks described in that patent may be modified to include features described in this document, and conversely the blocks 100/200 and other components described in this document may be modified to include features noted in the prior patent.

Exemplary dimensions for the blocks 100/200 are 1 inch thickness between the block faces 102/202, block sides 104/204 which are each 1.5 inches wide, and a central bore 106/206 having an average diameter of 1 inch. Exemplary dimensions for the fluid passages 112/212 and channels 116 are ½ inch, ¼ inch, and ⅛ inch. However, different dimensions could be used, and it is also possible to use different blocks 100/200 having different dimensions in the same fluid handling device; for example, different blocks 100/200 might be formed with 1 inch, 2 inch, and 4 inch thicknesses for use together in the same fluid handling device, with the 2 inch block effectively taking the place of 2 vertically stacked 1-inch blocks, the 4 inch block effectively taking the place of 4 vertically stacked 1-inch blocks (or 2 vertically-stacked 2-inch blocks), etc. Apart from having varying dimensions, the number and placement of features on the blocks may be changed, e.g., the number and placement of the fluid passages 112/212, and the configuration of features may change as well, e.g., the block bores 106/206 need not be circular.

As previously noted, the block faces 102/202 (and indeed the axial cross-sections of each block 100/200) are preferably shaped as tessellating regular polygons. A regular polygon is a polygon where all sides have the same size, and all of the interior angles are the same; examples are equilateral triangles, squares, pentagons, hexagons, etc. A tessellating regular polygon is a regular polygon wherein several polygons of the same size and type can fit snugly together in a side-by-side array which completely covers the area across which the polygons are arrayed; examples are triangles, squares, and hexagons. (Note that polygons other than regular polygons may tessellate, e.g., rectangles and parallelograms.) Symmetric tessellating regular polygons are those where each side has a parallel opposing side, e.g., squares and hexagons. These are particularly preferred shapes for blocks 100/200 since they allow block bores 106/206, fluid passages 112/212, fastener openings 110/210, and ducts 214 to extend between, and be symmetrically spaced about, opposing block faces 102/202 in such a manner that these apertures readily align when blocks 100/200 are stacked. In similar respects, channels 116 and other apertures extending from the block sides 104/204 (if included) can be formed to readily align when blocks 100/200 are horizontally arrayed.

The side fasteners 300 used to attach the blocks 100/200 together horizontally are depicted as having a circular closed annular form similar to a washer, though they may instead assume an open annular form (e.g., as a split ring, or a washer with a portion of its arc removed) and/or a non-circular form (such as an oval or square/rectangular form). The side fasteners 300 may be formed of any suitable materials, and can be rigid or flexible (as by forming them of elastomeric materials). The side fasteners 300 may include cutouts indented from their outer or inner circumferences to allow space for the insertion of a screwdriver head between a side fastener 300 and a block 100/200 to allow the side fastener 300 to be more easily removed from the depression 108/208 wherein it is fit (or alternatively, the semi-circular lands about which the side fasteners 300 are fit may include such cutouts).

The face fastener openings 110/210 are all preferably threaded and countersunk to accommodate bolt-like fasteners 302, with the face fastener openings on the block bottom faces (not shown) being identical to those on the block top faces 202. The fasteners 302 need not assume the form of bolts, and other forms of fasteners, such as threaded rods or smooth tie rods with threaded ends, could be used to vertically affix two or more blocks 100/200 together.

The block bores 106/206, fluid passages 112/212, channels 116, and ducts 214 preferably include countersunk depressions at their entry/exit locations on the block faces 102/202 and sides 104/204 so that O-rings 322, 324, and 326 (see particularly FIG. 2) can be fit about these conduits between horizontally adjoining blocks 100/200, thereby enhancing leak-resistant sealing. While the O-ring 326 is somewhat convoluted owing to its need to circumscribe the block bore 206, fluid passages 212, and ducts 214 of the intake/outlet blocks 200, simpler circular O-rings could be used (as with O-rings 322 and 324) if the ducts 214 do not extend to the block faces 202 (i.e., if the upper and lower bounds of the ducts 214 are spaced from the top and bottom block faces 202), and/or if appropriate plugs are inserted in the ducts at the top and bottom block faces 202. In this respect, the O-ring 326 could itself bear plugs between the circular portion bounding the bore 206 and the circular portions bounding the fluid passages 212, so that the O-ring 326 takes the form of a central circular O-ring joined to three surrounding circular O-rings by plugs, with the plugs being inserted in the tops and/or bottoms of the ducts 214 when the O-ring 326 is installed.

While only a single channel 116 is shown in one of the fluid passage blocks 100, it should be understood that the blocks 100/200 can, and often will, include one or more channels extending from their block sides 104/204 into the block bores 106/206, fluid passages 112/212, and/or ducts 214, with selected channels being fitted with plugs if their use is unnecessary.

Regarding the intake/outlet blocks 200, it was previously noted that the ducts 214 preferably extend in an at least partially tangential direction (i.e., in an at least partially clockwise or counterclockwise direction), and that all ducts 214 preferably have the same tangential orientation, so that fluid flowing from the fluid passages 212 to the block bore 206 (or conversely flowing from the block bore 206 to the fluid passages 212) will assume a circular or whirling motion in the block bore 206. This in turn can assist with more efficient pumping and/or power generation when the intake/outlet blocks 200 are used in combination with star wheels 400 and/or rotor discs 500. However, the ducts 214 need not all have the same tangential orientation; for example, some may be aligned in a clockwise direction and others may be aligned in a counterclockwise direction, for example, so that any fluid ejected from such ducts 214 into the block bore 206 will mix owing to the "collision" of their fluid flow streams in the block bore 206. It is also possible that intake/outlet blocks 200 may include multiple sets of ducts 214, with each set having different tangential orientations. As an example, a top portion of an intake/outlet block 200 (a portion nearer the block top face 202) might have ducts 214 with a clockwise orientation, and a bottom portion of an intake/outlet block 200 might have ducts 214 with a counterclockwise orientation.

Figure 2:
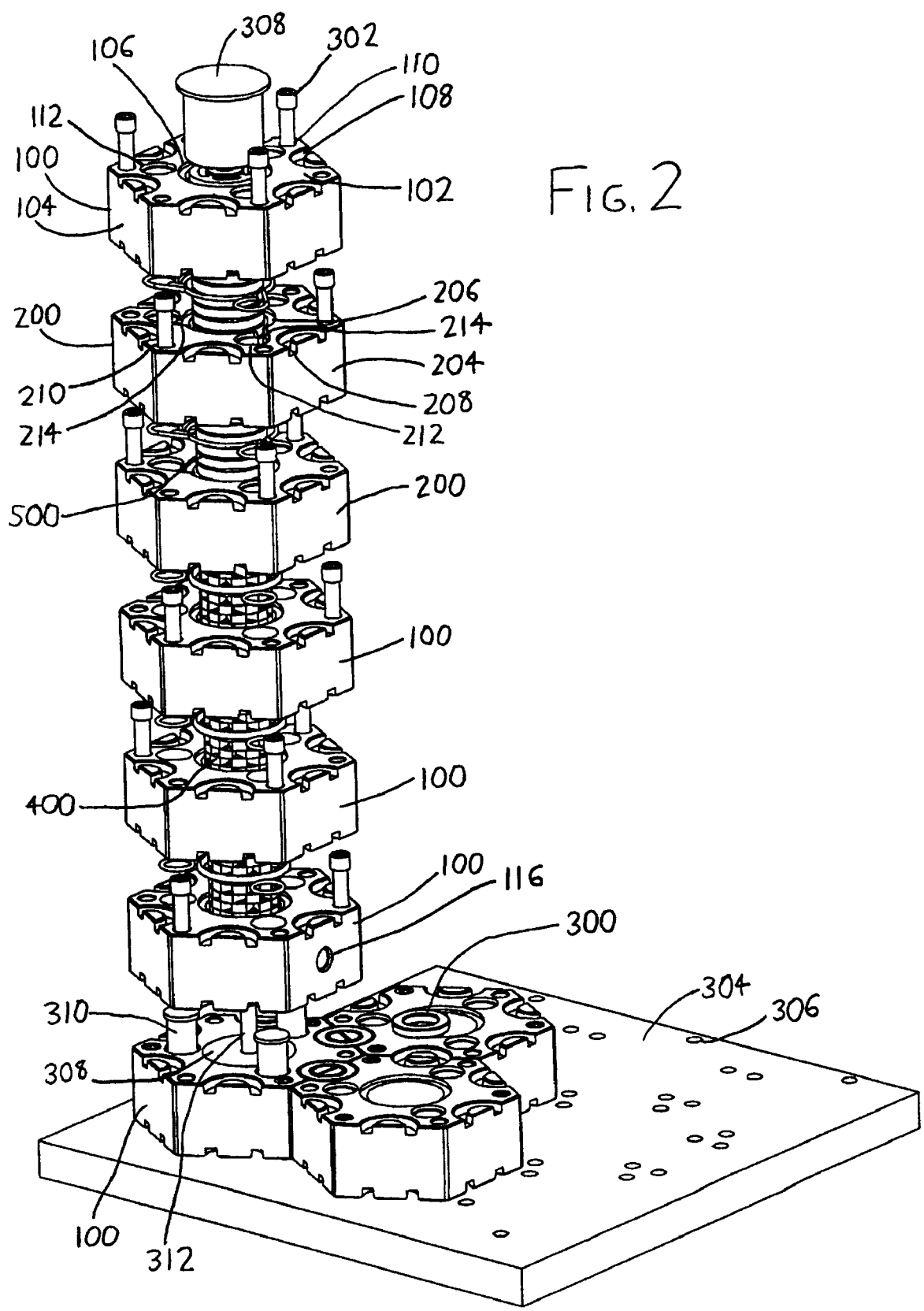
FIG. 2 provides an exploded perspective view of the exemplary fluid handling device of FIG. 1, showing the fluid passages 112/212 of the fluid passage blocks 100 and fluid intake/outlet blocks 200 (as well as the ducts 214 between the block bores 206 and the fluid passages 212 of the fluid intake/outlet blocks 200), and also showing the stacked star wheels 400 and rotor discs 500 within the block bores 106/206.
Figure 3:
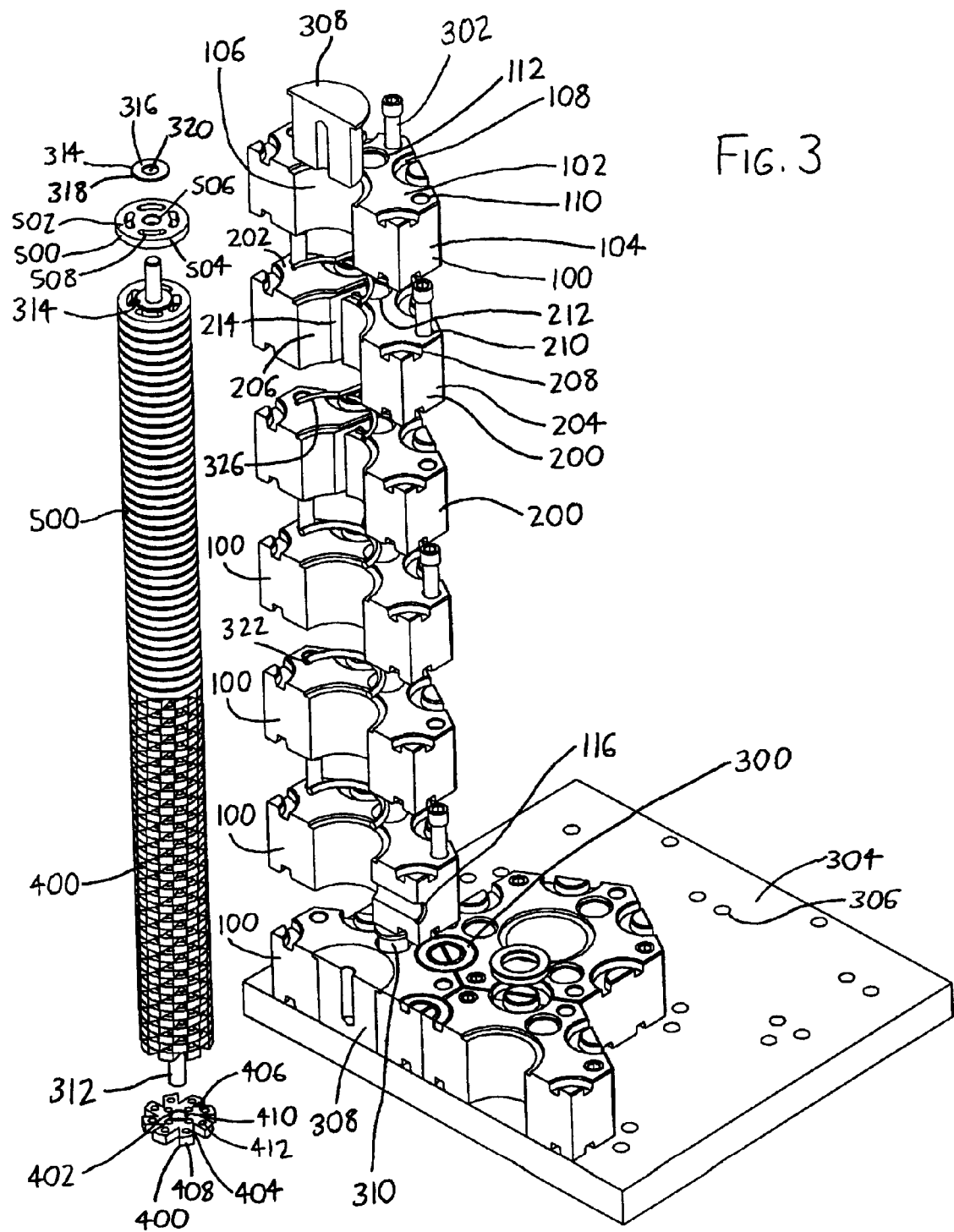
FIG. 3 provides a partially sectioned perspective view of the exemplary fluid handling device of FIGS. 1 and 2, showing the stacked star wheels 400 and rotor discs 500 (and spacers 314) on or adjacent to the shaft 312 and removed outwardly from the block bores 106/206.

The star wheels 400 depicted in FIGS. 2-3 are merely exemplary, and these may assume a wide variety of configurations apart from the ones shown. As examples, while the sides of the vanes 404 are angled tangentially (as best seen in FIG. 3), the vanes 404 could instead extend outwardly from the hub 402 with sides parallel to a radially oriented axis. The sides of the vanes 404 could alternatively or additionally be angled, curved, or twisted along their lengths in a propeller or helical gear-like fashion. The star wheels 400 might be modified to bear structure which interlocks as the star wheels 400 are stacked, so that all stacked star wheels 400 are restrained against relative rotation. The star wheels 400 need not have a planar configuration, and could (for example) have vanes 404 which are bent upwardly and/or downwardly, thereby possibly providing mixing effects as well as serving as a fluid impeller. The vane apertures 412 may vary in number and configuration, and if they are present, they need not be present on each vane 404. Vanes 404 could also or alternatively bear internal passages, e.g., leading from one vane aperture 412 to another; this feature, as well as some of the others noted above, can help generate frictional heating of fluids, such that the star wheels 400 serve as heaters as well as (or instead of) a pump or turbine, and/or as a mixer/agitator.

The rotor disks 500 may also vary in their dimensions and configurations, so long as they are effective to act, when stacked, as a bladeless pump or turbine. Exemplary configurations can be found, for example, in U.S. Pat. No. 1,061,142 to Tesla, as well as in later patents citing to this patent. Apart from varying in their configurations in much the same manner as the star wheels 400 discussed above, e.g., the rotor disks 500 could be formed with nonplanar faces, or with protruding vanes or roughened surfaces, to increase surface area; they could include spiral grooves or vanes to enhance pumping action; the location and configuration of the disk fluid passages 508 could be varied; etc. As discussed with respect to the star wheels 400 above, some of these features may assist in frictional heating of fluids, and may allow a rotor disk 500 to serve as a heater as well as (or instead of) a pump or turbine.

It should be understood that a wide variety of inserts serving as pumps/turbines could be used in place of the star wheels 400 and/or rotor disks 500, for example, a cylindrical insert wherein helical vanes spiral about a central shaft, or where helical passages spiral about a central shaft in the manner of an Archimedes' screw. However, the star wheels 400 and rotor disks 500 are particularly advantageous because their thin profile allows one or several wheels 400 and/or discs 500 to be stacked in the block bores 106/206 alongside other inserts. Additionally, they are readily stacked in varying configurations, e.g., star wheels 400 may be commingled between stacks of rotor disks 500, etc., and they can be stacked in such a manner that the functionality of the stack may change along the length of the shaft 312 (e.g., a portion may serve as a pump while another portion serves as a turbine, etc.).

The star wheels 400 and rotor disks 500 may be keyed or otherwise affixed to the shaft 312. The shaft 312 could bear a non-circular outer circumference which then complementarily fits within non-circular bores 410 and 506 of the star wheel 400 and rotor disk 500, thereby helping to prevent relative rotation between these components. It should be understood that the bore plugs 308 which bear the shaft 312 will often not be provided in the form of a simple solid plug, but will often bear motors or generators so that the shaft 312 can be driven for pumping action, or so that the shaft 312 may drive the generator to generate power.

It should be understood that an exemplary version of the invention has been shown and described above to illustrate preferred features of the invention. Apart from rearranging these features and/or omitting or adding them in different forms and combinations, other modifications are also considered to be within the scope of the invention. Following is an exemplary list of such modifications.

First, if desired, some or all of the fluid passages 112/212 could be tapped with internal threading so that components such as threaded input/output ports, gas traps, probe/sensor mounts, etc. can be more easily installed. The same modifications could be made to the block bores 106/206.

Second, other features noted in U.S. Pat. No. 7,146,999 to Giese et al. may be used with the components discussed above, e.g., closure plates (in essence, blocks which lack any bores 106/206 and fluid passages 112/212, and which block the flow of fluid). Other inserts described in that or other patents may be used as well, with examples being the heating discs noted in U.S. Pat. No. 5,341,768 to Pope, and the turbine/pump discs noted in U.S. Pat. No. 4,218,176 to Gawne.

The invention is not intended to be limited to the preferred versions described above, but rather is intended to be limited only by the claims set out below. Thus, the invention encompasses all different versions that fall literally or equivalently within the scope of these claims.

What is claimed is:

1. A modular fluid handling device comprising:
   a. a block having a series of block sides extending between a block top face and an opposing block bottom face, wherein the blocks may be arrayed together in side-to-side abutting relationship with other identical blocks to form a two-dimensional array of blocks, the block including:
      (1) a central block bore extending between the block faces, whereby the block may be arrayed with other identical blocks in face-to-face abutting relationship to form a stacked array of blocks wherein abutting blocks have their block bores coaxially aligned;
      (2) one or more ducts extending between the block bore and one or more of the block faces and sides;
   b. an elongated shaft centrally mounted within the block bore;
   c. at least one of:
      (1) a rotor disc having:
         (a) opposing disc faces;
         (b) an outer disc circumference radially bounding the disc faces, the disc circumference being complementarily fit within the block bore;
         (c) a disc bore centrally defined in, and extending between, the disc faces, the disc bore having the shaft received therein;
         (d) one or more disc fluid passages:
            (i) extending between the disc faces, and
            (ii) situated between the disc bore and the disc circumference;
      (2) a star wheel having:
         (a) a central hub having multiple vanes extending therefrom,
         (b) opposing wheel faces axially bounding the hub and vanes;
         (c) an outer wheel circumference radially bounding the vanes, the wheel circumference being complementarily fit within the block bore;
         (d) a wheel bore centrally defined in, and extending between, the wheel faces, the wheel bore having the shaft received therein.

2. The device of claim 1 wherein the ducts each open onto the block bore to extend in an axial direction along the block bore for at least substantially the entire distance between the block top face and the block bottom face.

3. The device of claim 1 wherein the ducts extend between the block bore and at least one of the block top and bottom faces without opening onto the block sides.

4. The device of claim 1 wherein the ducts extend from the block bore in directions oriented both radially and tangentially with respect to the block bore.

5. The device of claim 1 wherein the vanes of the star wheel include apertures extending between the opposing wheel faces.

6. The device of claim 1 wherein the vanes of the star wheel each have opposing vane sides extending between the opposing wheel faces, wherein at least one of the vane sides is oriented both radially and tangentially with respect to the wheel bore.

7. The device of claim 1 in combination with one or more spacers, each spacer having:
   a. opposing spacer faces;
   b. a spacer bore centrally defined in, and extending between, the spacer faces, the spacer bore having the shaft received therein;
   c. an outer spacer circumference radially bounding the spacer faces, the spacer circumference being sized with a radius less than the radius of:
      (1) the radius of the outer disc circumference, and
      (2) the radius of the outer wheel circumference.

8. The device of claim 1 wherein the block faces include semi-annular depressions extending from the block sides, whereby adjacent blocks arrayed together in side-to-side abutting relationship may receive an annular side fastener in their adjacent semi-annular depressions to affix the adjacent blocks together.

9. A modular fluid handling device comprising:
   a. a series of blocks, each having a block top face, an opposing block bottom face, and a series of block sides therebetween, wherein:
      (1) the block faces are shaped as tessellating regular polygons, whereby the blocks may be arrayed together in side-to-side abutting relationship to form a two-dimensional array of blocks;
      (2) each block includes a block bore extending between the block faces, whereby the blocks may be arrayed together in face-to-face abutting relationship to form a stacked array of blocks wherein abutting blocks have their block bores coaxially aligned;
   b. an elongated shaft;
   c. one or more rotor discs, each rotor disc having:
      (1) opposing disc faces axially bounding each rotor disc;
      (2) an outer disc circumference radially bounding the disc faces, the disc circumference being sized to be complementarily received within the block bore of one of the blocks;
      (3) a disc bore centrally defined in, and extending between, the disc faces, the disc bore being sized to complementarily receive the shaft;
      (4) one or more disc fluid passages:
         (a) extending between the disc faces;
         (b) situated between the disc bore and the disc circumference;
   d. one or more spacers, each spacer having:
      (1) opposing spacer faces axially bounding each spacer;
      (2) a spacer bore centrally defined in, and extending between, the spacer faces, the spacer bore being sized to complementarily receive the shaft;
      (3) an outer spacer circumference radially bounding the spacer faces, the spacer circumference being sized with a radius less than the radius between the disc bore and the disc fluid passages;
   e. one or more star wheels, each star wheel having:
      (1) a central hub having multiple vanes extending therefrom,
      (2) opposing wheel faces axially bounding the hub and vanes;
      (3) an outer wheel circumference radially bounding the vanes, the wheel circumference being sized to be complementarily received within the block bore of one of the blocks;

(4) a wheel bore centrally defined in, and extending between, the wheel faces, the wheel bore being sized to complementarily receive the shaft;

wherein:

A. the shaft may be installed within the block bores of one or more of the blocks, and B. one or more of the rotor discs, spacers, and star wheels may be installed on the shaft within the block bores to rotate therein.

10. The device of claim 9 wherein two or more rotor discs are included on the shaft with a spacer situated therebetween.

11. The device of claim 9 the star wheels each include apertures in their vanes, the apertures extending between the opposing wheel faces.

12. The device of claim 9 wherein one or more of the blocks are further defined as fluid intake/outlet blocks, wherein each fluid intake/outlet block further includes one or more ducts extending between the block bore and one or more of the block faces and sides.

13. The device of claim 9 wherein the block faces include semi-annular depressions extending from the block sides, whereby adjacent blocks arrayed together in side-to-side abutting relationship may receive an annular side fastener in their semi-annular depressions to affix the adjacent blocks together.

14. A modular fluid handling device comprising:

a. a series of blocks, each having a block top face, an opposing block bottom face, and a series of block sides therebetween, wherein:

(1) the block faces are shaped as tessellating regular polygons, whereby the blocks may be arrayed together in side-to-side abutting relationship to form a two-dimensional array of blocks;

(2) each block includes a central block bore extending between the block faces, whereby the blocks may be arrayed together in face-to-face abutting relationship to form a stacked array of blocks wherein abutting blocks have their block bores coaxially aligned;

b. one or more of the blocks are further defined as fluid passage blocks, wherein each fluid passage block further includes fluid passages:

(1) extending between opposing block faces;

(2) situated between the block bore and the block sides;

(3) regularly arrayed about the block bore such that a stacked array of fluid passage blocks having their block bores coaxially aligned have their fluid passages aligned, such that fluid may travel between the fluid passages of adjacent fluid passage blocks;

c. one or more of the fluid passage blocks are further defined as fluid intake/outlet blocks, wherein each fluid intake/outlet block further includes ducts extending from the fluid passages to the block bore, whereby fluid may travel between the fluid passages and the block bore.

15. The device of claim 14 wherein the ducts each include a slotted opening onto the block bore, the slotted opening being elongated along a direction oriented along the axis of the block bore.

16. The device of claim 14 wherein the slotted opening extends from the top block face to the bottom block face.

17. The device of claim 14 in combination with:

a. an elongated shaft situated along the axis of the block bore of one of the fluid intake/outlet blocks;

b. one or more star wheels, each star wheel having:

(1) a central hub having multiple vanes extending therefrom, (2) opposing wheel faces axially bounding the hub and vanes;

(3) an outer wheel circumference radially bounding the vanes, the wheel circumference being sized to be complementarily received within the block bore of the fluid intake/outlet block wherein the elongated shaft is situated;

(4) a wheel bore centrally defined in, and extending between, the wheel faces, the wheel bore having the shaft situated therein.

18. The device of claim 14 in combination with:

a. an elongated shaft situated along the axis of the block bore of one of the fluid intake/outlet blocks;

b. one or more rotor discs, each rotor disc having:

(1) an outer disc circumference radially bounding opposing disc faces, the disc circumference being sized to be complementarily received within the block bore of the fluid intake/outlet block wherein the elongated shaft is situated;

(2) a disc bore centrally defined in, and extending between, the disc faces, the disc bore having the shaft situated therein;

(3) one or more disc fluid passages:

(a) extending between the disc faces, and (b) situated between the disc bore and the disc circumference.

19. The device of claim 18 in combination with one or more spacers, each spacer having:

(1) opposing spacer faces axially bounding each spacer;

(2) a spacer bore centrally defined in, and extending between, the spacer faces, the spacer bore being sized to complementarily receive the shaft;

(3) an outer spacer circumference radially bounding the spacer faces, the spacer circumference being sized with a radius less than the radius between the disc bore and the disc fluid passages.

20. The device of claim 14 wherein the block faces include semi-annular depressions extending from the block sides, whereby adjacent blocks arrayed together in side-to-side abutting relationship may receive an annular side fastener in their semi-annular depressions to affix the adjacent blocks together.

* * * * *